(12) United States Patent
Jäger et al.

(10) Patent No.: US 8,129,360 B2
(45) Date of Patent: Mar. 6, 2012

(54) UTILIZATION OF PHOSPHATIDYLSERINE IN THE TREATMENT OF ATTENTION DEFICIT SYNDROME (ADHS)

(75) Inventors: Ralf Jäger, Freising (DE); Dirk Bökenkamp, Werne (DE)

(73) Assignee: Cargill Texturizing Solutions Deutschland GmbH & Co., KG, Hamburg (DE)

(*) Notice: Subject to any disclaimer, the term of this patent is extended or adjusted under 35 U.S.C. 154(b) by 824 days.

(21) Appl. No.: 10/491,636

(22) PCT Filed: Oct. 4, 2002

(86) PCT No.: PCT/EP02/11124
§ 371 (c)(1),
(2), (4) Date: Jun. 24, 2004

(87) PCT Pub. No.: WO03/030914
PCT Pub. Date: Apr. 17, 2003

(65) Prior Publication Data
US 2004/0235795 A1   Nov. 25, 2004

(30) Foreign Application Priority Data
Oct. 5, 2001  (DE) .................. 101 49 108

(51) Int. Cl.
*A01N 57/00*   (2006.01)
*A01N 57/26*   (2006.01)
*A61K 31/66*   (2006.01)
*A61K 31/685*  (2006.01)

(52) U.S. Cl. ............................. 514/75; 514/78
(58) Field of Classification Search ........... 514/75, 514/78
See application file for complete search history.

(56) References Cited

U.S. PATENT DOCUMENTS
| | | | | |
|---|---|---|---|---|
| 6,733,797 | B1* | 5/2004 | Summers | 424/728 |
| 6,964,969 | B2* | 11/2005 | McCleary | 514/283 |
| 7,208,180 | B2* | 4/2007 | Kiliaan et al. | 424/725 |
| 2004/0234587 | A1* | 11/2004 | Sampalis | 424/450 |

FOREIGN PATENT DOCUMENTS
| | | | |
|---|---|---|---|
| EP | 1 275 399 A2 | | 1/2003 |
| WO | WO0126642 | * | 4/2001 |
| WO | WO 01/78704 A3 | | 10/2001 |

OTHER PUBLICATIONS

Health & Medicine, Yale University, May 15, 2000. Persons with ADD have Complex Cognitive Problems. pp. 1-2.*
Conquer et al. 2000, Lipids vol. 35, No. 12, pp. 1305-1312.*
International Search Report for PCT/EP02/11124 of Jan. 31, 2003.
Kidd, Parris M., Ph.D., Attention Deficit/Hyperactivity Disorder (ADHD) in Children: Rationale for Its Integrative Management, Alternative Medicine Review, vol. 5, No. 5, 2000, pp. 402-428.
Brown, Atomoxetine and Stimulants in Combination for Treatment of Attention Deficit Hyperactivity Disorder: Four Case Reports, Journal of Child and Adolescent Psychopharmacology, vol. 14, 2004, p. 129-136.
Brown, Executive Functions and Attention Deficit Hyperactivity Disorder: Implications of two conflicting views, International Journal of Disability, Development and Education, vol. 53, 2006, p. 35-46.
Brown, ADD/ADHD and Impaired Executive Function in Clinical Practice, Current Attention Disorder Reports, 2009, p. 37-41.
Gammon et al., Fluoxetine and Methylphenidate in Combination for Treatment of Attention Deficit Disorder and Comorbid Depressive Disorder, Journal of Child and Adolescent Psychopharmacology, vol. 3, 1993, 10 pages.
Quinn et al., Docosahexaenoic acid supplementation and cognitive decline in Alzheimer disease: a randomized trial, JAMA, 2010; vol. 304, p. 1903-11 (Abstract only).
Wolraich et al., Attention-Deficit/Hyperactivity Disorder Among Adolescents: A Review of the Diagnosis, Treatment, and Clinical Implications, Pediatrics, vol. 115, 2005, p. 1734-1746.

* cited by examiner

*Primary Examiner* — Sreeni Padmanabhan
*Assistant Examiner* — Samira Jean-Louis
(74) *Attorney, Agent, or Firm* — Rothwell, Figg, Ernst & Manbeck, P.C.

(57) ABSTRACT

The invention concerns the use of phosphatidylserine (PS), lyso-phosphatidylserine or/and a physiologically acceptable salt thereof for the treatment of the attention deficit syndrome (ADHS) in small daily doses over a longer time period and in larger daily doses over a short period as well as in combination with suitable additives selected from the group comprising antioxidants, essential fatty acids, mineral substances, amino acids, mood-lifters or/and phospholipids. In this connection it is preferred to carry out the administration to probands aged 2 to 20 years preferably 3 to 10 years whereby the phosphatidylserine as well as the additives are used in solid and also in liquid formulations. Due to its positive properties phosphatidyl-serine is in particular suitable as a therapeutic agent or food supplement in connection with ADHS. The good tolerance of phosphatidylserine even in high doses and over a longer supplementation period and the excellent compliance should also be stressed.

14 Claims, No Drawings

UTILIZATION OF PHOSPHATIDYLSERINE IN THE TREATMENT OF ATTENTION DEFICIT SYNDROME (ADHS)

The present invention concerns the use of phosphatidylserine, lyso-phosphatidyl-serine or/and a physiologically acceptable salt thereof and the use of phosphatidyl-serine, lyso-phosphatidylserine or/and a physiologically acceptable salt thereof in combination with an additive to treat the attention deficit syndrome (ADHS).

The attention deficit syndrome (ADHS; attention deficit/hyperactivity disorder) is understood as a clinical syndrome which is characterized by a considerable impairment of the ability to concentrate and to sustain attention over long periods, disorders of impulse control and a facultative motoric hyperactivity and restlessness. In the past this syndrome was also referred to as "hyperkinefic syndrome" or "minimal cerebral dysfunction".

The clinical picture of ADHS is associated with neurobiologically defined changes in brain metabolism and in the neurotransmitters and is thus primarily a neurological clinical picture which can have major psychological sequelae (Swanson J M, Sergeant J A, Taylor E, Sonuga-Barke E J, Jensen P S, Cantwell D P, Attention-deficit hyperactivity disorder and hyperkinetic disorder, Lancet 1998; 351:429-33).

In the past years a special attention deficit syndrome without signs of motoric hyperactivity has been differentiated on the basis of recent investigations as the so-called inattentive type (Lahey B B; Carison C L, Validity of the diagnostic category of attention deficit disorder without hyperactivity: A review of the literature, Journal of Learning Disabilities 1991; 24:110-120). In the case of adults in which all typical symptoms of childhood are no longer detected, the additional designation "in partial remission" or "hyperkinefic syndrome residual type" has been proposed in the current DSM (Diagnostic and Statistical Manual of Mental Disorders.

The symptoms of the attention deficit syndrome in adults are still largely undescribed in Germany although the so-called hyperactivity syndrome or hyperkinetic syndrome is one of the most frequent psychiatric disorders in children and juveniles. Studies of the progress in these children have shown that there is a serious impairment persisting into adulthood which, among others, correlates with the occurrence of aggressive behavioural disorders and with antisocial personality disorders, addictive diseases and affective disorders (Mannuzza S, Klein R G, Bessler A, Malloy P, LaPadula M, Adult outcome of hyperactive boys, Arch General Psychiatry 1993; 50:565-76).

The proportion of ADHS in the population is nowadays estimated as 3-4% for children of primary school age and 2% for juveniles. The estimated proportion of all children, juveniles and adults that suffer from ADHS is 2-10%. Contrary to the view that the symptoms are lost in adulthood, up to 60% of the formally affected children are still found to have considerable impairments as juveniles.

ADHS is usually an initially purely biological predisposition which, however, can result in very different outcomes depending on the intensity and the personal circumstances of an individual's life.

According to current investigations it can be assumed that when the typical symptoms for this clinical picture are observed in patients whose symptoms have been attributed to a pure anxiety disorder or an impulsive, dissocial, hysterically eccentric or depressive disorder, at least an additional diagnosis of a hyperkinetic syndrome persisting into adulthood must be made.

Disorders of selective attention are typical as basic disorders of the attention deficit syndrome in which the affected individuals are at least not inattentive but rather attempt to follow several inner or outer sensations or thoughts simultaneously. Overall there is a major disorder in the self-control ability of these individuals which, in the case of reduced inhibition, can result in a failure of important executive functions in the area of wakefulness, regulation of emotion, cognitive functions, memory and planning actions.

Usually people can summon up a certain motivation and perseverance when carrying out unpleasant or boring tasks if something positive can be expected as a consequence. In persons with ADHS the converse is the case: a stimulation or activation is necessary at first in order that an activity can be begun at all.

The clinical result of a reduced inhibitory function in ADHS is on the one hand an excessive excitability or hypersensitivity and a disorder of impulse control which results in an increased distractibility or reduced attentiveness and reduced ability to concentrate.

According to the currently valid diagnosis criteria, symptoms of ADHS should have already manifested themselves before the age of 7.

Mild anomalies, delays in development e.g. in walking or speaking or disorders of perception or of fine motor functions often already occur in early childhood in ADHS children. So-called soft signs in the form of fine neurological peculiarities such as deviations in muscle tone or reflex and sensibility asymmetries have also been described which, among others, result in a conspicuously firm pressure or tenseness when writing resulting in poor handwriting. Bed-welting also occurs particularly frequently after the age of 7.

According to P. H. Wender (Attention Deficit Hyperactivity Disorder in Adults, Oxford University Press, 1995) the hyperactivity syndrome in childhood can be summarized as follows:

Hyperactivity or children that are above-average restless, nervous, cannot be stopped in their urge to talk, fidgety.

Attention deficits or reduced attention span, easily distracted.

The affected child does not reach the full achievement potential that he was thought to be capable of.

"Could if only he/she wanted to". Forgetfulness, problems with chain tasks and in following instructions and completing tasks.

In adulthood a feeling of not reaching all the goals that one has set out to achieve or a pronounced underachievement are in the foreground as the central symptom. Typical symptoms of ADHS in adulthood are for example also cognitive peculiarities, changes in the sustained attention span, disorders of working memory, hypersensitivity and impulsiveness, low tolerance to stress and impulsiveness, and also addictive behaviour or extreme stimulations in the form of for example an adrenalin kick, the classical hyperactivity and inability to relax.

The phosphatidylserine class of substances are phospholipids which occur naturally in the body and were previously grouped with the lysolecithins.

Phosphatidylserine supports numerous functions of body cells and occurs in naturally elevated concentrations in the brain were it supports the extremely sensitive functions of the nerve cells and the cells that are associated with them. Phosphatidyl-serine is a well-investigated substance which contributes to the well-being and health of living beings in all stages of life. Above all it exhibits a so-called anti-aging effect. Phosphatidylserine acts against stress, has an antidepressant effect and it even in a certain way has a rejuvenating effect. With its ability to improve memory, its anti-depressant action and its ability to lower stress hormones in the blood, phosphatidylserine is one of the most important of all nutrients for the brain.

Phosphatidylserine as a food supplement like the other phospholipids has a favourable effect on health which is not only in a direct manner. Phosphatidylserine can equally improve the uptake of numerous other food substances or food supplements or act synergetically with them. This was proven in clinical double-blind studies.

As a phospholipid, phosphatidylserine is an important component of cell membranes. These very thin flexible three-dimensional structures with their phospholipid components are an important matrix for enzyme systems which, among others, regulate or maintain the energy balance of the cells and thus ensure that the body cells work together smoothly.

Furthermore it is known that phosphatidylserine supports the brain in generating energy, that it has a positive effect on cell/cell connections (synapses), it amplifies the effect of chemical transmitter substances such as acetylcholine, dopamine, noradrenalin and serotonin resulting in an improved cognitive capacity of the brain such as concentration, learning ability, shortterm memory and word memory.

Phosphatidylserine is also an important agent against ageing processes in the brain which has now been demonstrated by about 18 double-blind studies and over 40 published studies in humans. Moreover phosphatidyl-serine has also been said to have the ability to at least partially reverse memory losses associated with ageing processes.

A drug treatment can also be carried out for the therapy of ADHS in addition to other forms of therapy. A first attempt to treat ADHS patients with phosphatidylserine has been described in the prior art. In this experiment small dosages of 100 mg per day were firstly used over a period of 2 months. This treatment did not result in a clear improvement of the symptoms. Subsequently higher dosages were administered over a period of 4 months (200 to 300 mg daily, in the case of severe symptoms up to 500 mg daily). This treatment with high dosages had a positive effect in 25 of 27 probands aged from 3 to 19 years which exhibited all typical ADHS symptoms. In one proband (7 years, female) only a slight improvement was achieved, in another proband (15 years, female) it was not possible to make a clear statement about an improvement (Dr. Parris Kidd, Clear Viewpoint towards ADHS: PS, Lecture presented at the 11th Food Design Show, Tokyo Big Sight, Tokyo, Japan, Sep. 20, 2000). In this experiment no side effects occurred with drugs that were administered at the same time but the dosages used were relatively high.

Hence the object of the present invention was to provide an agent based on phosphatidylserine to treat the attention deficit syndrome (ADHS) with the aim of achieving a good physiological tolerance and a good compliance with no side effects at an efficient dosage.

Another object of the invention was to provide further efficient dosage forms with regard to the amount and duration of the administration of phosphatidylserine for the treatment of ADHS.

This object was achieved by the use of phosphatidylserine, lyso-phosphatidylserine or/and a physiologically acceptable salt thereof alone or in combination with an additive. The term phosphatidylserine (PS) as used herein encompasses all compounds belonging to the phosphatidylserine class of substances including the lyso compounds and the corresponding salts. Examples of these are among others phosphatidyl-L-serine or lyso-phosphatidyl-L-serine.

It was surprisingly found that PS exhibits synergistic effects in combination with other substances when used to treat ADHS. Hence the present invention concerns the use of phosphatidylserine (PS), lyso-phosphatidylserine or/and a physiologically acceptable salt thereof in combination with an additive to produce an agent for treating the attention deficit syndrome (ADHS). The term "treatment" as used herein encompasses the treatment as well as the prevention of ADHS.

The use according to the invention of PS enables on the one hand a reduction of the PS dose and, on the other hand, a reduction of the treatment period. Moreover the result of using phosphatidylserine according to the invention was that there was no limitation whatsoever on its wellknown good tolerance even at high doses and over a long supplementation period, compliance with phosphatidylserine was not a problem and also no habituation effects occurred in probands with ADHS. Furthermore PS as used according to the invention develops its positive effect in ADHS to a significantly greater extent than the previously known drugs.

When using a combination of phosphatidylserine (PS) and an additive according to the invention it has proven to be advantageous when the phosphatidylserine is administered in daily doses of 20 to 1000 mg, preferably of 50 to 600 mg.

Daily doses of 1 to 10,000 mg, especially of 5 to 5000 mg and in particular of 50 to 1000 mg are suitable for the additive or the mixture of additives.

In this connection an administration over a period of at least 7 days and preferably not longer than 6 months is suitable and the respective supplementation periods can be readily repeated and completely without problems after pauses or/and a readjustment of the daily dose. In this connection the period of 7 days does not necessarily have to be a consecutive sequence of days.

Suitable additives for the use according to the invention include antioxidants, essential fatty acids, mineral substances, amino acids, antidepressants, phospholipids or/and mixtures thereof. The said additives have a particularly positive effect on brain function: antioxidants protect in particular tissues or organs that are supplied intensively with oxygen; essential fatty acids and phospholipids support and maintain the function of cell membranes and nerve cells or nerve tissue which occur in particular in the brain; mineral substances and in particular magnesium and calcium also have an important function in neuronal processes.

Preferred antioxidants are for example bioflavonoids, vitamin E, vitamin C, $\alpha$-lipoic acid or/and carotinoids. $\omega$-3 and $\omega$-6 fatty acids and particularly preferably decosahexaenoic acid (DHA) and $\gamma$-linolenic acid (GLA) are examples of suitable essential fatty acids. Suitable amino acids are for example essential amino acids or/and amino acid derivatives such as creatine. Magnesium and calcium are examples of preferred mineral substances. Extracts of St'John's wort, kava kava or/and mixtures thereof are particularly preferably used as mood-lifters. Preferred phospholipids are for example phosphatidylcholine (lecithin), phosphatidic acid, phosphatidylethanolamine or/and phosphatidylinositol.

In addition to the use of phosphatidylserine (PS) and suitable derivatives thereof in combination with an additive, another subject matter of the present invention is the use of phosphatidylserine, lyso-phosphatidylserine or/and a physiologically acceptable salt thereof without a further additive to produce an agent for treating the attention deficit syndrome (ADHS). In this case administration is over a maximum period of 2 months in preferred daily doses of 150 to 600 mg or/and over a period of more than 2 months, preferably of more than 3 months and particularly preferably of more than 4 months in which case suitable daily doses are 50 to 150 mg.

In the case of the use according to the invention of phosphatidylserine it was surprisingly found that the use of phosphatidylserine (PS) in low dosages over a long period and in higher dosages over a short period is very suitable for the treatment of ADHS symptoms, contrary to the previous state of the art.

This use according to the invention of phosphatidylserine also showed that it was well tolerated even in high doses and over a longer supplementation period, there was a good compliance and also in this case no habituation effects occurred in ADHS patients.

It has also proven to be very advantageous when the longer term phosphatidylserine administration (over more than 2 months) is preferably carried out in daily doses of 50 to 150 mg and more preferably in daily doses of 100 to 150 mg. In the case of a short-term administration of phosphatidylserine over a period of no more than 2 months, daily amounts of 150 to 600 mg and preferably of 250 to 450 mg have proven to be particularly suitable.

Since phosphatidylserine is an endogenous substance it is in general metabolized very rapidly and completely and therefore already develops its good effect after a very short "accumulation time". Nevertheless 7 days which do not necessarily have to be consecutive is regarded as a minimum period for ADHS treatment with PS in the embodiments of the present invention. According to the invention 6 months is regarded as the upper limit for the regular intake of phosphatidylserine for ADHS, but the supplementation period can be readily repeated several times and completely without problems after pauses or/and a readjustment of the daily dose.

A clientele of probands has proven to be suitable for the use according to the invention of phosphatidylserine (derivatives) to treat ADHS which are aged between 2 and 20 years whereby an age between 3 and 10 years has proven to be particularly suitable not least in order to prevent later irreparable chronic symptoms and in the interest of an unproblematic compliance.

According to the invention phosphatidylserine (PS), suitable derivatives thereof, lyso-phosphatidylserine or/and a physiologically acceptable salt thereof can be used in solid as well as in liquid formulations to treat ADHS in all embodiments.

Suitable solid formulations are for example powder, chewing, sucking and effervescent tablets, dragees and capsules and, in view of the usually young age of the preferred probands, sweets or chocolate bars. Juices and soft drinks are for example particularly suitable as liquid formulations.

According to the invention the formulation can additionally contain physiologically acceptable or/and physiologically effective additives or/and formulation adjuvants. Suitable physiologically acceptable or/and physiologically effective additives for the use according to the invention are for example antioxidants, members of the essential fatty acids, antidepressants (e.g. mood-lifters, preferably of plant origin such as St. John's wort or kava kava), probiotics, various phospholipids of PS or the natural brain substance dimethylaminoethanol (DMAE) and alcohols, sugars, vitamins, trace elements, amino acids, neurotransmitters, stimulants, colourings and flavourings. Furthermore combinations of phosphatidylserine with the previously known drugs or other drugs that are effective for ADHS that have an additive or synergistic effect can be used. If this results in synergistic effects, the respective effective PS doses can be advantageously lowered and the respective daily amount can then be matched to body indices such as size and weight especially in the case of children and juveniles.

Suitable formulation adjuvants for the use according to the invention are for example carbohydrates (e.g. methylcellulose), $SiO_2$, stearates, solubilizers, flavourings, preservatives and separation agents as well as texturants.

Due to the fact that it is well tolerated physiologically and has a significant effect in the attention deficit syndrome, phosphatidylserine (PS) is very well suited especially as a therapeutic agent or food supplement within the scope of the present invention and, particularly in the latter case, the dosage can be kept small and it can also be administered over long periods.

The following examples 1 to 4 illustrate the effectiveness and compliance when using phosphatidylserine (PS) or phosphabdylserine (PS) in combination with an additive according to the invention.

EXAMPLES

Probands in an open study (examples 1 to 4) were selected with the aid of the Wender Utah Rating Scale (WURS) on the basis of their performance at school as well as clinical and physiological tests.

They were assessed after 4, 6 and 8 weeks with the short-term supplementation and after 2, 4 and 6 months with the longer supplementation. The probands were examined for measurable differences with regard to concentration, attention, impulsivity, aggression potential and hyperactivity. Questionnaires were used to involve probands, parents and teachers in the evaluation.

Example 1

150 mg phosphatidylserine and 100 mg of a mixture of vitamin E, vitamin C, DHA and GLA were administered every second day to a 9 year old schoolgirl over a period of 9 weeks. Positive trends were already noticeable after 4 weeks; there was a clear positive effect after 6 weeks. The attentiveness, concentration and memory performance as well as achievement at school improved considerably.

Example 2

200 mg phosphatidylserine was administered three times daily to a 14 year old schoolboy over a period of 7 weeks. A marked decline in hyperactivity was observed at the end of the supplementation; moreover the proband reported that there was an improvement of general well-being.

Example 3

100 mg phosphatidylserine per day was administered over a period of 6 months to an 8 year old schoolboy. An improvement of general well-being and an uplift in mood was observed after the third month. The attentiveness, concentration and memory performance as well as achievement at school improved considerably.

Example 4

400 mg phosphatidylserine in combination with 100 mg of a mixture containing DHA, St. John's wort and vitamin E and C was administered daily for 8 weeks to an 11 year old schoolboy. A clear improvement of the general well-being, reduced aggression and improved achievements at school were already observed after a short supplementation.

The invention claimed is:

1. A method of treatment of a patient of age 2 to 20 years suffering from attention deficit syndrome (ADHS) comprising daily administering to said patient an ADHS-treating effective amount of a blend of compounds, the blend consisting of:
   a phosphatidyl compound selected from the group consisting of phosphatidylserine (PS), a physiologically acceptable salt thereof, lyso-phosphatidylserine, a physiologically acceptable salt thereof, and mixtures thereof; and
   an additive selected from one or more essential fatty acids, the blend having a daily dosage of from 50 to 600 mg of phosphatidyl compound and from 50 to 1000 mg of additive.

2. The method of treatment as claimed in claim 1, wherein the essential fatty acid is selected from the group consisting of ω-3 and ω-6 fatty acid.

3. The method of treatment as claimed in claim 2, wherein the essential fatty acid is selected from the group consisting of decosahexaenoic acid (DHA) and y-linolenic acid (GLA).

4. The method of treatment as claimed in claim 1, wherein the administration is carried out for a maximum of 2 months with a daily dose of 150 to 600 mg of the phosphatidyl compound.

5. The method of treatment as claimed in claim 4, wherein the daily dose of the phosphatidyl compound is 250 to 450 mg.

6. The method of treatment as claimed in claim 1, wherein the administration of the blend is carried out for a period of more than 2 months with a daily dose of 50 to 150 mg of the phosphatidyl compound.

7. The method of treatment as claimed in claim 6, wherein the daily dose of the phosphatidyl compound is 100 to 150 mg.

8. The method of treatment as claimed in claim 6, wherein the administration is carried out for no more than 6 months.

9. The method of treatment as claimed in claim 6, wherein the blend is administered as a formulation which is in a form which is selected from the group consisting of a solid, a liquid and mixtures thereof.

10. The method of treatment as claimed in claim 1, wherein the administration is carried out for a period of at least 7 days.

11. The method of treatment as claimed in claim 1 wherein the treatment is for not more than 2 months with the daily dose of phosphatidyl compound of from 150 to 600 mg.

12. The method of treatment as claimed in claim 1 wherein the treatment is for more than 3 months with the daily dose of phosphatidyl compound of from 50 to 150 mg.

13. The method of treatment as claimed in claim 1, wherein the blend is administered as a therapeutic agent, food supplement, functional food or special diet.

14. The method of treatment as claimed in claim 1, wherein the treatment is provided for humans of age 3 to 10 years.

* * * * *